US010960174B2

United States Patent
Ranta et al.

(10) Patent No.: US 10,960,174 B2
(45) Date of Patent: Mar. 30, 2021

(54) SYSTEM AND METHOD FOR MONITORING PERSONAL HEALTH AND A METHOD FOR TREATMENT OF AUTONOMIC NERVOUS SYSTEM RELATED DYSFUNCTIONS

(71) Applicant: MERU HEALTH OY, Helsinki (FI)

(72) Inventors: Kristian Ranta, Helsinki (FI); Albert Nazander, Helsinki (FI); Markus Palonen, Helsinki (FI)

(73) Assignee: Meru Health Oy, Helsinki (FI)

( * ) Notice: Subject to any disclaimer, the term of this patent is extended or adjusted under 35 U.S.C. 154(b) by 0 days.

(21) Appl. No.: 16/341,453

(22) PCT Filed: Apr. 26, 2018

(86) PCT No.: PCT/FI2018/050303
§ 371 (c)(1),
(2) Date: Apr. 12, 2019

(87) PCT Pub. No.: WO2018/197754
PCT Pub. Date: Nov. 1, 2018

(65) Prior Publication Data
US 2019/0358427 A1 Nov. 28, 2019

(30) Foreign Application Priority Data
Apr. 28, 2017 (FI) .................................... 20175377

(51) Int. Cl.
A61M 21/02 (2006.01)
A61B 5/04 (2006.01)
(Continued)

(52) U.S. Cl.
CPC ........... *A61M 21/02* (2013.01); *A61B 5/0205* (2013.01); *A61B 5/04001* (2013.01);
(Continued)

(58) Field of Classification Search
CPC ... A61B 5/4035; A61B 5/4029; A61B 5/0205; A61B 5/04001; A61B 5/0476;
(Continued)

(56) References Cited

U.S. PATENT DOCUMENTS 6,212,427 B1 * 4/2001 Hoover ................ A61B 5/0006
600/515
7,647,234 B1 * 1/2010 Ruderman .......... G06F 19/3418
705/2
(Continued)

FOREIGN PATENT DOCUMENTS

EP 2862509 A1 4/2015
WO WO2008002941 A2 1/2008
(Continued)

OTHER PUBLICATIONS

Basta et al: "Chronic insomnia and stress system", Sleep Med Clin. Jun. 2007, vol. 2 (2), pp. 279-291.
(Continued)

*Primary Examiner* — Erin M Piateski
(74) *Attorney, Agent, or Firm* — Laine IP Oy (57) ABSTRACT

A system and method of monitoring the health of a person. The system comprises at least one sensor capable of measuring at least one physiological signal generated by the autonomic nervous system of the person for providing measurement data, and a data processing system which is configured to store a reference indicator, to receive measurement data from the sensor during a plurality of consecutive health-maintenance sessions in order to collect a plurality of measurement data sets corresponding to said health-maintenance sessions, to determine at last one health indicator based on the measurement data sets, said at least one health indicator being sensitive to physiological state of or changes in the autonomic nervous system, and to compare the at least one health indicator with said reference indicator.

(Continued)

Objective information on autonomic nervous system related dysfunctions is retrieved which allows for systematic treatment to the person.

26 Claims, 4 Drawing Sheets

(51) Int. Cl.
*A61B 5/00* (2006.01)
*G16H 50/30* (2018.01)
*A61B 5/0205* (2006.01)
*A61B 5/0476* (2006.01)
*A61B 5/024* (2006.01)

(52) U.S. Cl.
CPC ............ *A61B 5/0476* (2013.01); *A61B 5/486* (2013.01); *A61B 5/7275* (2013.01); *A61B 5/742* (2013.01); *A61B 5/7405* (2013.01); *G16H 50/30* (2018.01); *A61B 5/02405* (2013.01); *A61M 2205/50* (2013.01); *A61M 2205/52* (2013.01); *A61M 2230/06* (2013.01); *A61M 2230/10* (2013.01); *A61M 2230/50* (2013.01); *A61M 2230/63* (2013.01)

(58) Field of Classification Search
CPC ......... A61B 5/16; A61B 5/486; A61B 5/7275; A61B 5/7405; A61B 5/742; A61M 21/02; G16H 10/20; G16H 20/70; G16H 50/30; G16H 50/70
USPC ........................................................ 600/301
See application file for complete search history.

(56) References Cited

U.S. PATENT DOCUMENTS

| | | |
|---|---|---|
| 2006/0178588 A1 | 8/2006 | Brody |
| 2010/0174205 A1 | 7/2010 | Wegerif |
| 2011/0245633 A1* | 10/2011 | Goldberg ............... A61B 5/681 600/301 |
| 2012/0071731 A1 | 3/2012 | Gottesman |
| 2012/0289791 A1 | 11/2012 | Jain et al. |
| 2014/0058279 A1 | 2/2014 | Shinba |
| 2014/0141395 A1 | 5/2014 | Gavish et al. |
| 2016/0113526 A1 | 4/2016 | Nageshwar et al. |
| 2016/0379668 A1 | 12/2016 | Greig et al. |
| 2017/0071551 A1 | 3/2017 | Jain et al. |
| 2017/0251967 A1* | 9/2017 | Premsukh ............ A61B 5/0004 |
| 2017/0325700 A1* | 11/2017 | Lane ..................... G16H 50/30 |

FOREIGN PATENT DOCUMENTS

| | | |
|---|---|---|
| WO | WO2015049644 A1 | 4/2015 |
| WO | WO2016061513 A1 | 4/2016 |

OTHER PUBLICATIONS

Cortelli et al: "Autonomic dysfunction in sleep disorders", MedLink, Jul. 21, 2003.
InformedHealth.org [Internet]. Cologne, Germany: Institute for Quality and Efficiency in Health Care (IQWiG); 2006-. Depression: How effective are antidepressants? Jan. 28, 2015 [Updated Jan. 12, 2017]. Available from: https://www.ncbi.nlm.nih.gov/books/NBK361016/.
Sohrab Saeb et al: "Mobile Phone Sensor Correlates of Depressive Symptom Severity in Daily-Life Behavior: An Exploratory Study", J Med Internet Res. Jul 2015. vol. 17(7). e175, pp. 1-11.
Yoshino et al: Proceedings of Measuring Behavior, Maastricht, 2008.

* cited by examiner

SYSTEM AND METHOD FOR MONITORING PERSONAL HEALTH AND A METHOD FOR TREATMENT OF AUTONOMIC NERVOUS SYSTEM RELATED DYSFUNCTIONS

PRIORITY

The present application is a U.S. National Stage Entry under 35 U.S.C. 371 of International Patent Application No. PCT/FI2018/050303, filed on Apr. 28, 2018, and claims the benefit of Finnish Application FI20175377, filed on Apr. 28, 2017.

FIELD

The invention relates to a health monitoring system and method of monitoring the health of a person. In particular, the invention relates to monitoring of autonomic nervous system related dysfunctions. In addition, the invention relates to a treatment method utilizing the present monitoring system or method.

BACKGROUND

Depression treatment relies currently on paper based (self-report) diagnosis of depression which is very inaccurate and produces "one-size-fits-all" treatment for people, which again leads to poorly effective treatment. It is said that most commonly used methods for treating depression: antidepressants and Cognitive Behavioural Therapy produce desired results with roughly 40% of people.

There is an ongoing paradigm shift in mental healthcare, moving towards 'precision medicine in mental health'. This can be achieved by individualizing care for each person based on their physiological, behavioral or other particular features which can be measured and which data can be analysed to create an individual care plan.

It has also been studied that treating these psychological dysfunctions improves the health of the person also from a physiological standpoint, not just psychologically.

The connection between sleep and the autonomic nervous system has been studied in the medical research field. For example, Cortelli at al., in "Autonomic dysfunction in sleep disorders", *MedLink*, Jul. 21, 2003, suggest that sleep and the autonomic nervous system are closely related from an anatomical, physiological, and neurochemical point of view and that sleep disorders may cause or be associated with clinically relevant autonomic dysfunctions.

It has also been suggested that there is a correlation between mood during daily life and autonomic nervous system activity during sleep (Yoshino et al., Proceedings of Measuring Behavior, Maastricht, 2008) and that several psychological and physiological factors contribute to the onset and perpetuation of insomnia (Basta et al., *Sleep Med Clin.* 2007 June; 2(2): 279-291.).

The research suggests that autonomic nervous system dysfunction is connected to poor sleep or hypersomnia.

There are medical professionals and therapists that are experts in diagnosis, monitoring and treatment of autonomic nervous system related dysfunctions, such as those mentioned above. For the public, however, detecting and monitoring, not to speak about treatment of such dysfunctions is relatively difficult and costly since typically continued personal therapy sessions and subjective assessment of symptoms and progress are needed.

On the other hand pharmachotherapies may be effective but often cause unwanted side effects and on a population level are relatively poorly performing, cf. Yoshino et al, *Proceedings of Measuring Behavior*, Maastricht, 2008.

SUMMARY OF THE INVENTION

It is an aim of the invention to provide a system and method for monitoring personal health. One aim is to provide a monitoring system and monitoring method which provide objective information on autonomic nervous system related dysfunctions and therefore to allow for systematic and personalized treatment actions.

It is also an aim to provide a novel method of treatment of autonomic nervous system related dysfunctions.

A further aim is to provide a system that supports both self-maintenance of health and professional advice.

The present invention relies on the basic finding that there is a connection between psychological dysfunctions such as stress, anxiety and depression and the autonomic nervous system.

Further, in the invention there is an understanding that several objective measures can be used to create an accurate picture of a person with depressive (or other mental illness related) symptoms. These types of measures can be brain electricity (EEG) patterns or HRV data revealed patterns (indicators of autonomic nervous system state). Other objective measures such as person's mobile phone accelerometer data (activity, step count etc) or features of written or spoken language of a person (semantic analysis), can be analysed to better understand the person and to create an individual treatment plan for optimal results.

The invention is based on the use of a sensor that is capable of measuring at least one physiological signal reflecting or correlating with the state of the autonomic nervous system of the person for providing measurement data and using the sensor during a plurality of consecutive health-maintenance sessions in order to collect a plurality of measurement data sets. The data sets are analyzed to determine health indicators that reflect the physiological state and development of the autonomic nervous system.

In particular, it is possible to determine a reference indicator, such as a target health indicator, through measurements, whereby the session-based health indicator can be compared with the reference indicator to gain knowledge of the health-maintenance sessions have the desired effect.

The present system for monitoring the health of a person typically comprises
- at least one sensor capable of measuring at least one physiological signal generated by the autonomic nervous system of the person for providing measurement data,
- data processing system configured to
  - store a reference indicator,
  - receive measurement data from the sensor during a plurality of consecutive health-maintenance sessions in order to collect a plurality of measurement data sets corresponding to said health-maintenance sessions,
  - determine at last one health indicator based on the measurement data sets, said at least one health indicator being sensitive to physiological state of or changes in the autonomic nervous system, and
  - compare the at least one health indicator with said reference indicator.

In particular, the data processing system may store a health-monitoring session plan that can be changed if the comparison suggests that a previous plan is not proceeding as desired.

The present method of monitoring the health of a person comprises

> determining a session plan and storing the session plan in a data processing system,
> measuring at least one physiological signal generated by the autonomic nervous system of the person during a plurality of consecutive health-maintenance sessions according to the session plan stored in a data processing system,
> collecting into the data processing system a plurality of measurement data sets corresponding to said health-maintenance sessions, and
> operating the data processing system for
>> determining at last one health indicator based on the measurement data sets, said at least one first health indicator being sensitive to physiological state of or changes in the autonomic nervous system, and
>> comparing the at least one health indicator against predefined comparison criteria,
>> changing the session plan depending on the outcome of the comparison.

The present method of treating autonomic nerve system related dysfunctions of a person, > providing at least one sensor capable of measuring at least one physiological signal generated by the autonomic nerve system of the person,
> providing a data processing system capable of storing and processing measurement data provided by the sensor,
> operating the sensor and data processing system during a plurality of health-maintenance sessions according to a session plan for collecting measurement data sets corresponding to said sessions,
> determining at least one first health indicator based on the measurement data sets, said first health indicator being sensitive to physiological changes in the autonomic nerve system, and
> determining if the temporal development of the first health indicators fulfills predefined criteria, and, in the affirmative,
>> changing the session plan,
>> operating the sensor and data processing system during a plurality of further health-maintenance sessions according to the changed session plan for collecting further measurement data sets corresponding to said further sessions.

More specifically, the invention is mainly characterized by what is stated in the characterizing parts of the independent claims.

Considerable advantages are attained by the present invention. Thus, depending on the sensor(s) and indicator(s) chosen, the present system and methods can be used to characterize several different autonomic nerve system related dysfunctions that are caused by or manifested as sleep disorders, stress, depression or chronic pain, and to guide the user towards right exercises for self-maintenance of health. In particular, a personal long-term health-monitoring and/or dysfunction treatment program may be planned and conducted utilizing the system and methods.

Next, embodiments of the invention are described in more detail with reference to the attached drawings.

EMBODIMENTS

Definitions

The term "health-maintenance session" refers to a session where the person conducts activities that has or supposedly has effects on his or her health and in particular reflected in physiological changes of the autonomic nervous system. A health-maintenance session can, in particular, be a meditation session, exercise session, controlled breathing session, resting session or sleeping session (referred to as "type" of session). A health maintenance program includes a plurality of health-maintenance sessions, as well as evaluation of results.

The "Autonomic nervous system" stands for the system of nerves and ganglia that innervates the blood vessels, heart, smooth muscles, viscera, and glands and controls their involuntary functions, consisting of sympathetic and parasympathetic portions.

A "session plan" is a data structure capable of defining the types and/or times and/or durations and/or any other contents of health-maintenance sessions. A session plan can include sessions of one type only or sessions of many types. Changing of a session plan comprises adding or removing sessions or changing any of the parameters of any existing sessions.

An "indicator" (as in first/second health indicator or health trend indicator) refers to a parameter or index, a set of parameters or indices, or a function, generally speaking any characterizing data that depends on the measurement data and describes the physiological state of or changes in the autonomic nervous system based on the measurement data. In other words, a health indicator is sensitive to physiological state of or changes in the autonomic nervous system. An indicator may be computed based on a single session data set ("single session indicator") or a plurality of session data sets ("trend indicator" or "session-to-session indicator"). The indicator can be e.g. a heart beat (HR) heart rate variability (HRV) index or HRV trend (computed based on heart rate data) or brain activity index or brain activity trend (computed based on EEG data).

"First health indicator" refers to an indicator computed based on single session data, representing current state of the autonomic nervous system. For example, the first health indicator can be an HRV index value or some other value averaged over a selected portion of a measurement data set from a single session.

Examples of other indicators, which can be processed as "first health indicators" are self-report data, smart-phone sensor data, data provided by an accelerometer, a thermometer, or a light sensor for tracking amounts of light, as well as audio input, or air pressure changes, sleep sensor data, exercise sensor data, written or spoken data from the person, such as. text analysis. Any data of which relate to the status of the individual and which can be used for tailoring his treatment program can be utilized.

In this respect reference can be made to findings that features extracted from mobile phone sensor data, including GPS and phone usage, provide behavioral markers that are related to depressive symptom severity: Sohrab Saeb et al., "Mobile Phone Sensor Correlates of Depressive Symptom Severity in Daily-Life Behavior: An Exploratory Study", *J Med Internet Res.* 2015 July; 17(7): e175.

In embodiments, combinations of a various indicators are used.

In preferred embodiments, HRV is used as an indicator optionally together with one or more indicators listed above.

"Second health indicator" refers to an indicator computed based on single session data using different temporal regions thereof, such as data measured at the start (first half) and end (second half) of the session, therefore representing short-term temporal variation of data and fast reacting of the autonomic nervous system to session activities. For example, the second health indicator can be proportional to the difference between a first HRV index (or some other value) at the beginning of a session and a second HRV index (or some other value) at the end of a session.

Similar computed indicators can be provided for the other indicators listed above in connection with the first health indicators.

"Health trend indicator" refers to an indicator computed based on multiple session data either directly or using previously computed first and/or second health indicators. A health trend indicator therefore represents slow changes in the autonomic nervous system, typically in the scale starting from 4 weeks to 12 months. For example, the health trend indicator can be a slope of a line fitted to several first or second health indicator values, therefore describing the rate of changes in the autonomic nervous system.

"Reference indicator" is an indicator typically determined before the actual monitoring or treatment program or at least using data collected before the start of the program. The reference indicator can reflect the state of the autonomic nervous system before the monitoring program (i.e. "pre-monitoring indicator") or, for example, a target state to which the program aims at (i.e. "target indicator"). The reference indicator can be defined automatically using pre-monitoring measurement data or manually or semi-automatically by a therapist having access to the pre-monitoring measurement data.

"Comparing" the at least one health indicator with said reference indicator covers all actions that utilizes both these indicators, typically yielding a result that depends on the difference between the indicators.

"Heart rate variability (HRV) index" means an index that describes the variation of heart beat-to-beat interval.

"Brain activity index" refers to an index that describes the level or nature of electric activity of one or more sections of the brain.

In the present technology, a system is provided for monitoring the health of a person.

Typically, the system comprises one or more sensors capable of measuring physiological signals generated by the autonomic nervous system of the person for providing measurement data.

There is also provided a data processing system configured to store a reference indicator; to receive measurement data from the sensor during a plurality of consecutive health-maintenance sessions in order to collect a plurality of measurement data sets corresponding to the health-maintenance sessions; and to determine at last one health indicator based on the measurement data sets. In particular, the health indicator is sensitive to physiological state of or changes in the autonomic nervous system.

The data processing system is finally configured to compare the one or more health indicators with the one or more reference indicators.

The health indicator typically comprises a plurality of first health indicators separately determined based on each measurement data set and representing the state of the autonomic nervous system.

This kind of indicators may be used as such to give feedback on the state of the autonomic nervous system for the person through automatic analysis or therapist-aided analysis, or for computing e.g. a trend indicators describing long-term temporal development of the state of the autonomic nervous system.

In the present context, the term "therapist" is to be given a broad interpretation, cover also other professionals in the healthcare field.

Thus, health indicator data are retrieved more frequently or less frequently, or in different ways, depending of the patient's condition. The actual retrieval of data can be made dependent on the indicator data obtained. If, for example, preset criteria are fulfilled during the program, e.g. if the condition of the patient is worsening, it is possible to shorten the intervals between measuring sessions to ensure that treatment is adapted to the patient's condition and gravity thereof and made efficient. By contrast, improvement in the patient's condition can be reflected in longer intervals between retrieval of indicator data so as to reduce intervention.

In some embodiments, the at least one health indicator comprises a plurality of second health indicators separately determined based on each measurement data set and representing temporal variation of measurement data within said measurement data sets.

This kind of indicators may also be used as such to give feedback on the short term response of the autonomic nervous system for the person through automatic analysis or therapist-aided analysis, or for computing e.g. a trend indicators describing long-term temporal development of the short-term response capability of the autonomic nervous system.

Is some embodiments, the at least one health indicator comprises a health trend indicator determined based on a plurality of measurement data sets from a plurality of health-maintenance sessions, for example using the first and/or second health indicators. The data processing system may, for example, be configured to determine the temporal health trend indicator based on the plurality of first or second health indicators and time values associated therewith.

In some embodiments, the comparison comprises determining if the health indicators have changed at a predefined rate using the reference indicator, using data one the times of conducting the health-maintenance sessions. The trend indicator may be used in this process.

In some embodiments, the method comprises collecting at least one pre-monitoring data set during at least one first pre-monitoring health session before said health-maintenance sessions and determining the reference indicator based on the pre-monitoring data set. When the measurement data sets have been collected, the reference indicator can be used as the comparison criteria, or part thereof, to evaluate whether the target of the monitoring or treatment program have been achieved.

In some embodiments, the data processing system comprises at least two user accounts having access to monitoring data of the person, the first user account allowing storage of measurement data sets and the second user account allowing reading of measurement data sets and/or health indicators. In further embodiments, collecting the data sets is carried out using the first user account and evaluation of the data and giving feedback for the user and/or changing the session plan is carried out using the second user account.

In some embodiments, the monitoring system comprises a storage medium comprising first software means executable on a computer, such as mobile computing device, the first software means being functionally connectable with the sensor. The first software means comprises computer-executable instructions for performing said step of receiving, and optionally one or more of the steps of storing the measurement data sets, determining indicators and comparing of indicators. The first software means may also comprise computer-executable instructions for providing visual or audial guidance for the person on conducting the health-maintenance sessions.

In some embodiments, the monitoring system further comprises second software means executable on a cloud data server, so that the first and the second software means are capable of exchanging data over a network connection. The second software means comprise computer-executable instructions for performing at least one, typically all, of the steps of storing the measurement data sets, determining indicators and comparing of indicators.

The system may further comprise user access control means in the first and/or second software means capable of containing at least a first and second user access levels, wherein the first access level authorizes the person to initiate data collection for said health-maintenance sessions, and the second user access level authorizes another person to define said reference indicator and/or to define a session plan for the person conducting the health-maintenance sessions. The second user access level also may authorize access to the measurement data sets and/or the health indicators and/or the result of the comparison.

In typical embodiments, the system is suitable for collecting at least four measurement data sets from separate health-maintenance sessions over a period of at least four weeks, such as at least six sets over a period of six weeks.

Turning next to the working embodiments according to the drawings, the following can be noted.

Figure 1A:
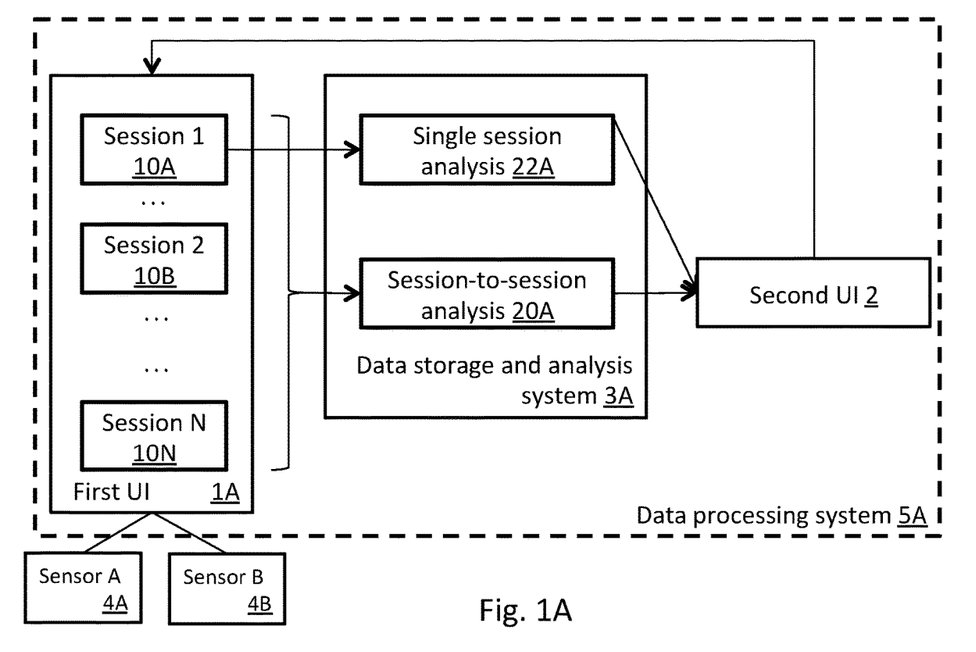
FIG. 1A shows schematic block representation of the system and method according to one embodiment of the invention.

FIG. 1A depicts one embodiment of the present system in a general level. The system comprises a data processing system 5A comprising a first user interface (UI) 1A, which is capable of collecting measurement data from a plurality of sessions 10A, 10B, ... 10N using one or more sensors 4A, 4B. The first UI 1A is accessible by the person to be monitored or treated. The data collected is processed in a data storage and analysis system 3A. There may be provided means for conducting a session-to-session analysis 20A and/or single session analysis 22A. The data fed to the data storage and analysis system 3A and/or produced therein is accessible to a second UI 2. The second user interface 2 is accessible by a professional therapist, who may study the data and give feedback to the person, typically in the form of data feed used by the first UI 1A.

The professional feedback may be in the form of notifications, changes to the session plan, or educational material (text/audio/video), to mention some examples. Thus, a structured treatment program, remotely supervised by a professional therapist, is formed.

Figure 1B:
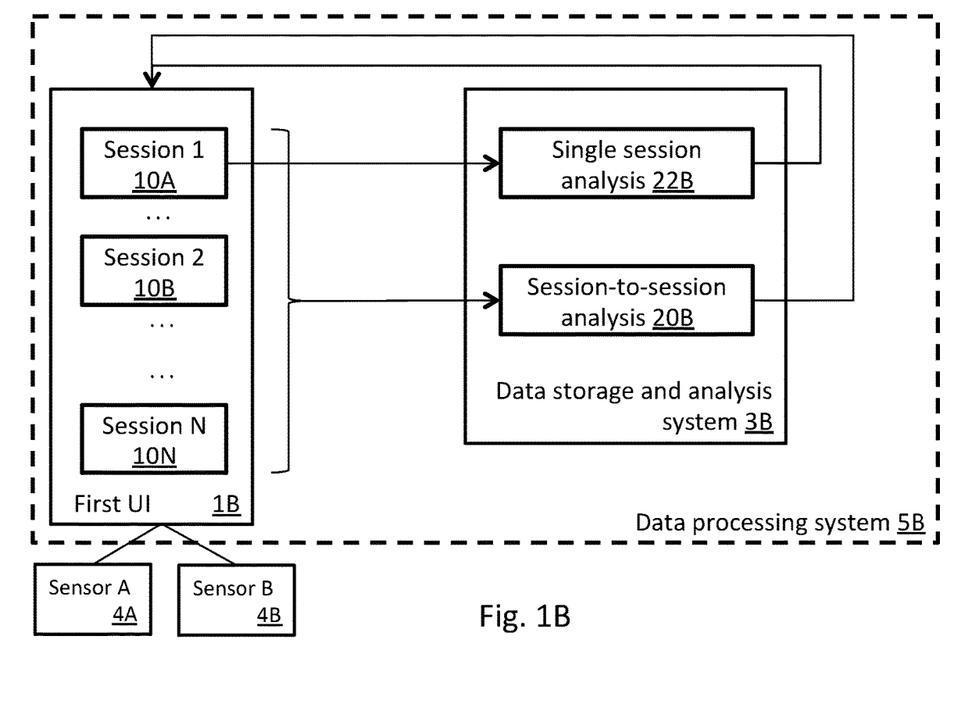
FIG. 1B shows schematic block representation of the system and method according to another embodiment of the invention.

FIG. 1B shows an alternative system with a first UI 1B and data storage and analysis system 3B capable of conducting session-to-session data analysis 20B and/or single session data analysis 22B. In this example, the analysis or analyses 20B, 22B result in automated feedback to the first UI 1B.

The embodiments of FIGS. 1A and 1B can also be combined, i.e., both automated feedback and a second user interface plus professional feedback may be possible with the same system.

The first UI 1A comprises software means containing the session plan, controls the sensor or sensors used to measure the session data sets, and associates the data sets to the respective sessions. Typically, the software means is in the form of a mobile application executable in a mobile device, such as smart phone or a smart watch or other wearable device. In particular, the first UI may be implemented with the first software means referred to above.

In one embodiment, the first UI 1A is capable of controlling HR and/or EEG-measurement process for a patient to evaluate status and/or progress of depression or anxiety or chronic pain decline and progress of positive meditative or treatment effects, as reflected in the heart rate and/or in the brain waves.

The data processing system 5A may be a centralized or distributed system.

The data storage and analysis system 3A can be run in the same device as the first UI 1A or, for example, on a data server, which is functionally connected to the first UI 1A. As discussed later in more detail, in a typical setup, the first UI 1A is run in a mobile device and the data storage and analysis system 3A is implemented at least partly in a network server. The second UI 2 can be run either as a mobile application or network server application. Thus, the second UI 2 can comprise a mobile application or a desktop interface connected with the data storage and analysis system 3A. In one embodiment, the second UI 2 is a dashboard software program that is capable of displaying all patients connected to a single therapist with their measurement and/or analysis data.

In one embodiment, the session-to-session analysis results in an indicator representing a developing profile of heart rate, heart rate variability or brain activity status or changes therein. The profile can be a trend indicator calculated from the change of measurement data over time, i.e. from session to session. For example, the trend data of morning-to-morning stationary measurements (e.g. HR and/or EEG measured 2-10 minutes at a time) can be calculated and analyzed to reliably see changes in physiology.

In one embodiment, also data on the starting point and the end point of a session are used to calculate a single session trend indicator. More generally speaking, the system may be configured to calculate one or more second health indicator descriptive of temporal variation of measurement data within one or more single measurement data sets. The second health indicator may be calculated, for example, by comparing first measurement data contained in the first half of a measurement data set, corresponding to the first half of a health-maintenance session, and a second measurement data contained in the second half of a measurement data set, corresponding to the second half of the health-maintenance session.

The health indicator or indicators, whether in the form of a single index, set of parameters or more complex function, and whether based on single session data or multiple session data, can be used either automatically or by a professional therapist to adjust the session plan and treatment individually.

The system may also be adapted for carrying out at least one operation selected from the group of storing, displaying and communicating over a data network, of the indicators and any result of indicator evaluation, such as comparison with a reference indicator.

Figure 2:
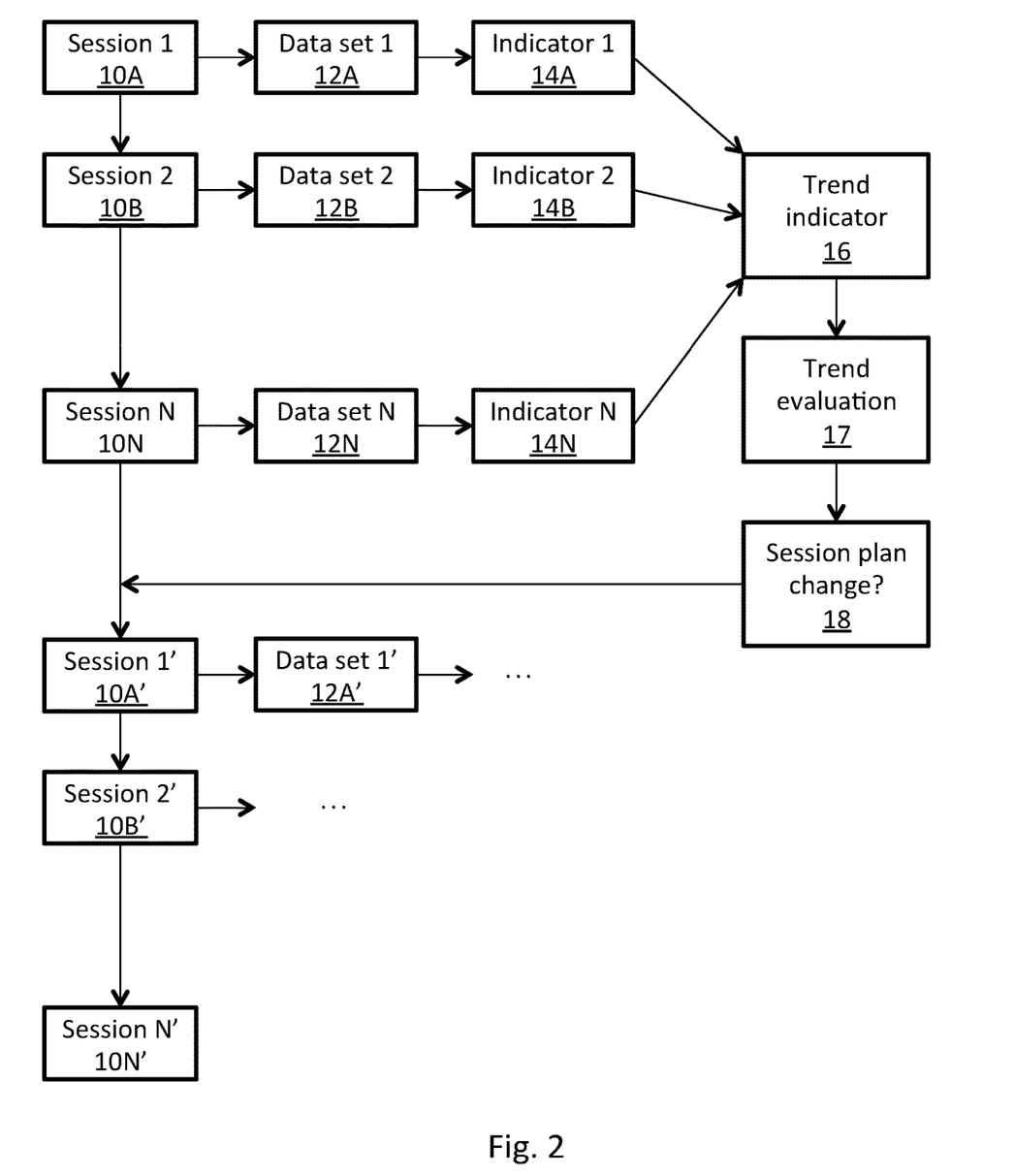
FIG. 2 illustrates in detail data analysis according to one embodiment of the invention.

FIG. 2 illustrates a multi-session data collection and processing system in more detail.

As will appear, the user carries out, according to a session plan, a plurality of health-maintenance sessions 10A, 10B, . . . 10N, from which data is collected as data sets 12A, 12B . . . 10N, respectively. Based on each data set 12A, 12B, . . . 12N, at least one single-session indicator 14A, 14B, . . . 14N, is calculated, respectively. The single-session indicators 14A, 14B, . . . 14N are used to determine a temporal trend indicator 16. The trend indicator 16 is evaluated in step 17, which typically includes comparison with a predefined reference indicator to see if the sessions have had a desired effect. If there is a need to change the session plan, it can be changed in step 18, after which the user continues, in a similar fashion, with the changed plan (sessions 10A', 10B', . . . 10N') to collect further data sets 12A' . . . until the monitoring program ends.

In some embodiments, the data processing system is configured to collect, in addition to the actual session data sets, one or more pre-monitoring data sets during one or more first pre-monitoring health session before said health-maintenance sessions and to use the pre-monitoring data set for determining said reference indicator. Using of the pre-monitoring data set may comprise determining a pre-monitoring health indicator based on the pre-monitoring data set and computing the reference indicator based on the pre-monitoring health indicator and storing reference indicator. Alternatively or in addition to that the pre-monitoring data or any value derived therefrom may be sent to the second UI used for example by a therapist, and the reference indicator associated with the pre-monitoring data may be received from the second UI.

In some embodiments, the system is configured to store at least one reference time value associated with the pre-monitoring data set or any reference indicator derived therefrom. In addition, the system is configured to associate a health-maintenance session time value to each health indicator derived from the actual measurement data sets. When evaluating the progress, the comparison of the indicators may include determining if the health indicator has changed at a desired rate using the reference indicator, the health-maintenance session time values and the reference time value.

In one example, the system is configured to associate a health-maintenance session time value to each health indicator and to determine a temporal health trend indicator based on the first health indicators and the time values associated therewith. Further, the health trend indicator may be displayed and/or compared with a reference health trend indicator.

The system may also comprise means for providing feedback for the person on the during a session based on the measurement data, in particular based on a health indicator calculated therefrom. For example, audio feedback or neuro feedback may be provided to the user based on single session HR and/or EEG (or skin conductance sensor) data to further affect brains to learn the right kind of session practicing technique.

According to some embodiments, the data storage and analysis system is adapted to collect and analyze measurement data sets and/or first/second health indicators or trend indicators from health-maintenance sessions of a plurality of different persons for obtaining population data. The population data can be used to give instructions as input for further individualization instructions to patient via the first UI and/or displayed to therapist via the second UI for decision making support.

In some embodiments of the present system and method, the sensor comprises a heart rate (HR) sensor, the physiological signal comprises a heart rate signal, and the first health indicator comprises a heart rate variability (HRV) indicator.

The heart rate sensor can be based on any HR measurement technology, such as electric measurement (typically a chestband), optical measurement (typically wristband or ear clip) or pressure sensor. The heart rate sensor is used to determine in particular heart rate variability (HRV), which in turn can be used
- as a measure of physiological stress state of the body, correlating with e.g. depression, anxiety and chronic pain, and/or
- to provide the patient with a feedback-loop
    - for meditation exercises (how well body responds to meditation),
    - for controlled breathing exercises or combinations thereof, and
- to provide the therapist with physiological and objective data on patient program adherence and program effectiveness, as well as how well patients are learning different techniques for health-maintenance or improvement In some embodiments of the present system and method the sensor comprises an electroencephalographic (EEG) sensor, the physiological signal comprises an EEG signal, and the first health indicator comprises a brain activity indicator.

The EEG sensor can be an EEG headband capable of measuring brain activity at a plurality of measurement points. EEG data can be used
- to measure meditation related brain changes and meditation training progress, and/or
- be used to measure depression and anxiety intensity and quality, and/or
- to provide the patient and healthcare professional with an objective feedback loop, and/or
- for neurofeedback for improving training effectiveness.

The sensor is preferably connected to the mobile application serving as the first user UI via a wireless or wired communication channel. Also several different types of sensors either within single sessions or in different sessions, to provide more representative data on the autonomic nervous system.

Figure 3:
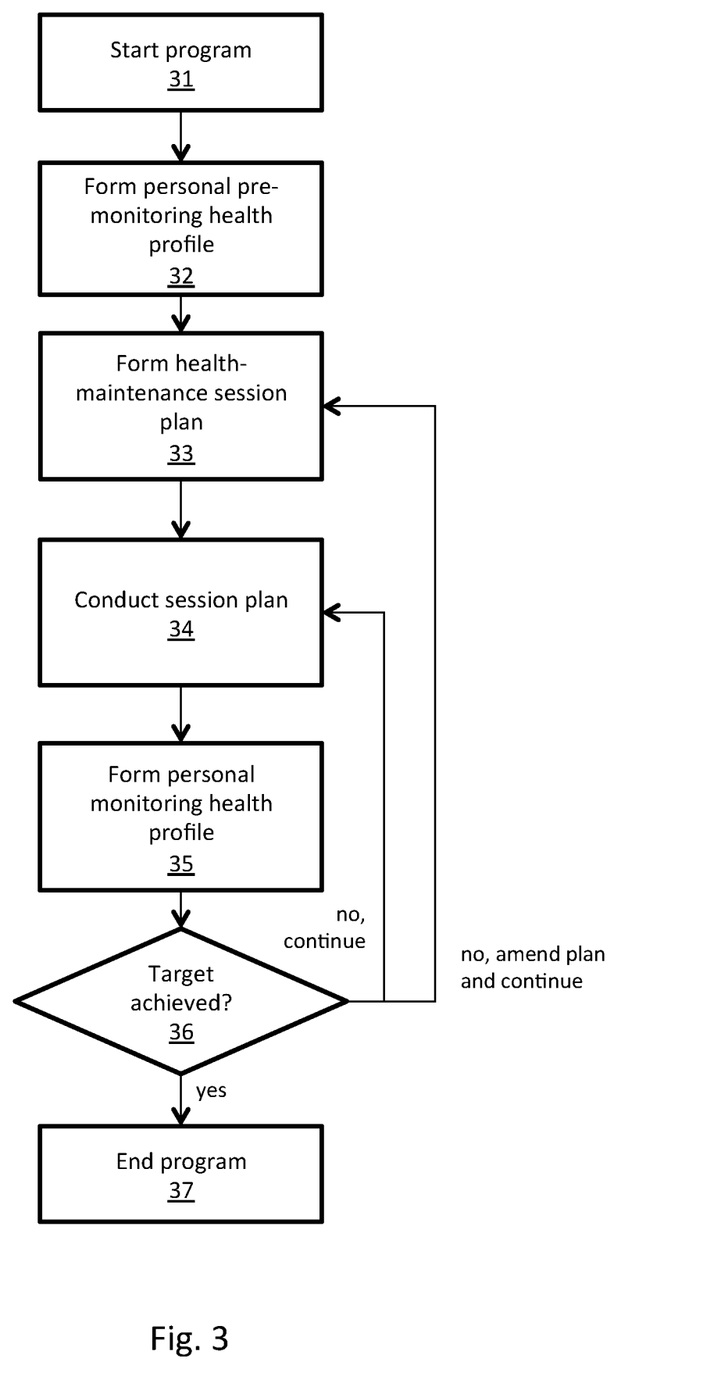
FIG. 3 depicts a personal health-monitoring program that can be carried using the present system and method.
Figure 4A:
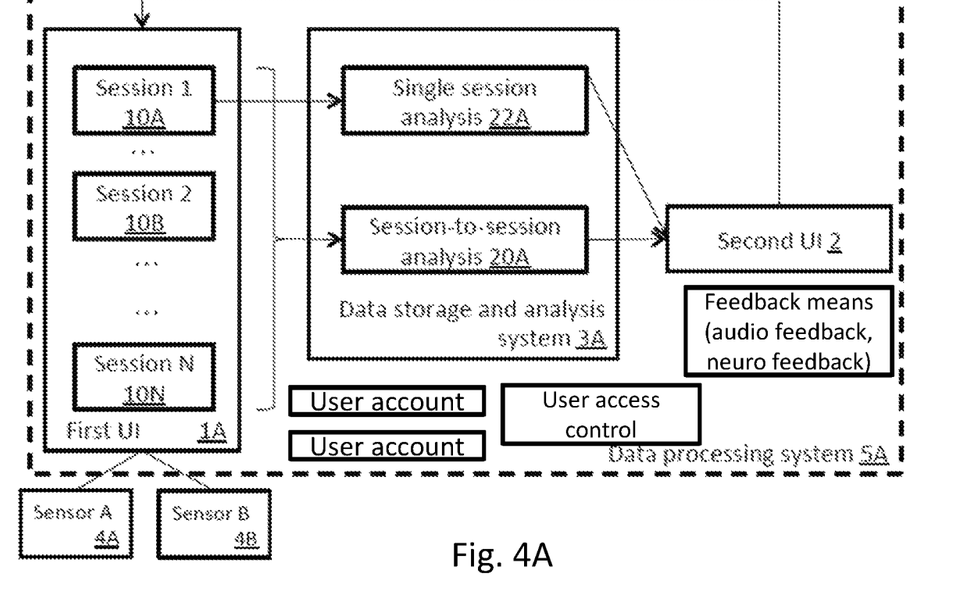
FIG. 4A shows schematic block representation of the system and method according to one embodiment of the invention.
Figure 4B:
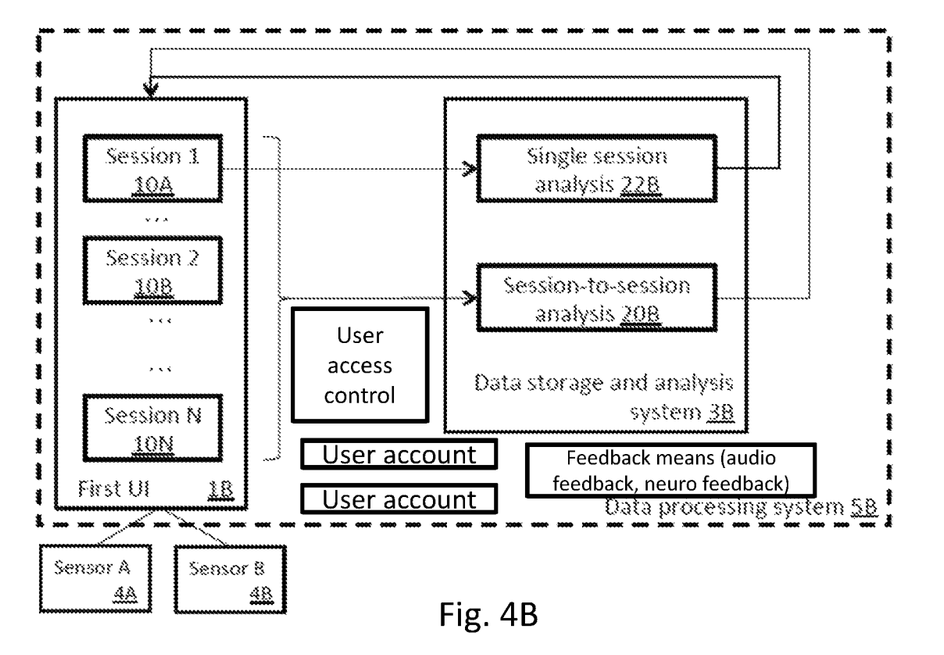
FIG. 4B shows schematic block representation of the system and method according to another embodiment of the invention.

FIG. 3 illustrates exemplary basic steps of a health-monitoring program. In step 31, a participant starts the program. In step 32, a pre-monitoring health profile is formed. This typically involves measurements using the same monitoring setup as used later in the program and forming a session plan for the participant to conduct during the program. Also a target for the program, for example in the form of a reference indicator based on the measurements can be determined. In one embodiment, forming the pre-monitoring profile involves collecting of biosignal or other form of individual data during a plurality of days and/or from a plurality of pre-monitoring sessions using e.g. wearable sensors and/or questionnaires. After that, a profile is formed for the participant based on his/her personal data collected. The individual profile indicates specific characteristics in person's behavior and/or physiology and helps to customize the program and upcoming exercises, i.e. the session plan.

In step 34, the participant conducts the session plan determined. Typically, this part of the program lasts for several weeks or months. When the plan has been followed for a predefined time or sessions, or after each health-maintenance session, a monitoring heath profile is formed in step 35, the monitoring profile being comparable with the pre-monitoring profile.

In step 36, it is compared if a target of the program is achieved, after which the program can either be ended, continued as such or continued with amended session plan. In case of changes, a new profile can be formed at the end of the program, or during the program one or more times, to assess the situation.

Next, two examples of potential program participants, their pre-monitoring health profiles and session plans are given.

Person A
Starting Profile (Pre-Monitoring Profile)
   Male, 50 years old
   HRV (rMSSD) average over 4 resting state measurements: 45 (significantly lowered vs. average healthy person: 65)
   Sleep data indicating excessive sleep (avg. over 7 days over 9 hours/night)
   Activity data indicating reduced activity (average less than 3000 steps/day)
   Self-report data indicating severe depressive symptoms (PHQ-9 score of 21)
Treatment Plan
   Short (5-10 minutes) daily paced breathing sessions to improve autonomic nervous system state
   Weekly behavioral activation focused therapy to improve severe depression symptoms and get patient activated
   Daily therapist chat and weekly calls focused on these areas Person B
Starting profile (pre-monitoring profile)
   female, 30 years old
   HRV (rMSSD) average over 4 resting state measurements: 60 (moderately lowered vs average healthy person: 80)
   Sleep data indicating inadequate sleep (average under 7 hours/night)
   Activity data indicating a lot of activity (average >10000 steps/day)
   Self-report data indicating mediocre depressive symptoms (PHQ-9 score of 14)
Treatment Plan
   Medium length (10-20 minutes) to long (20-40 minutes) meditation sessions prior to bed-time
   Deep breathing exercises to address potential co-morbid anxiety symptoms
   Cognitive behavioral therapy exercises and lessons to improve understanding of harmful thought patterns and behaviors
   Weekly therapist chat and monthly calls focused on these areas It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

Acronyms

UI user interface
HRV heart rate variability
HR heart rate
EEG electroencephalography

REFERENCE SIGNS LIST 1A, 1B, 2 user interface (UI)
10A, 10B, . . . sessions
10A', 10B' . . . sessions
3A, 3B data storage and analysis system
4A, 4B sensors
5A data processing system
12A, 12B . . . data sets 12A', 12B' . . . modified data sets
14A, 14B, . . . single-session indicator
16 temporal trend indicator
17 evaluation step
18 change step
20A, 20B session-to-session analysis
22A, 22B single session analysis
31 step for starting the program.
32 a pre-monitoring health profile forming step
34 step in which session plan is conducted
35 monitoring heath profile forming step

CITATION LIST

Non-Patent Literature

Cortelli at al., *MedLink*, Jul. 21, 2003.
Yoshino et al, *Proceedings of Measuring Behavior*, Maastricht, 2008.
Basta et al., *Sleep Med Clin.* 2007 June; 2(2): 279-291.
Sohrab Saeb et al., *J Med Internet Res.* 2015 July; 17(7): e175.

The invention claimed is:

1. A system for monitoring the health of a person, the system comprising:
 at least one sensor capable of measuring at least one physiological signal generated by an autonomic nervous system of the person for providing measurement data, and
 a data processing system configured to
  store a reference indicator,
  receive measurement data from the sensor during a plurality of consecutive health-maintenance sessions in order to collect a plurality of measurement data sets corresponding to said health-maintenance sessions,
  determine at least one first health indicator based on the measurement data sets, said at least one first health indicator being sensitive to a physiological state of or changes in the autonomic nervous system of the person, and
  compare the at least one first health indicator with said reference indicator,
 wherein
  the at least one first health indicator comprises a plurality of second health indicators separately determined based on each measurement data set and representing temporal variation of measurement data within said measurement data sets, and
  the data processing system is configured to calculate the second health indicators based on
   first measurement data contained in the first half of a measurement data set, corresponding to the first half of a single health-maintenance session, and
   second measurement data contained in the second half of a measurement data set, corresponding to the second half of the single health-maintenance session,
 wherein the data processing system is configured to store a health-monitoring session plan which is changed based on the comparison of the at least one first health indicator with the reference indicator,
 wherein the health maintenance-session is a single meditation session, a single exercise session, or a single controlled breathing session.

2. The system according to claim 1, wherein the at least one first health indicator comprises a plurality of health indicators separately determined based on each measurement data set and representing a state of the autonomic nervous system.

3. The system according to claim 1, wherein the at least one first health indicator comprises a health trend indicator determined based on a plurality of measurement data sets from a plurality of health-maintenance sessions.

4. The system according to claim 3, wherein said measurement data sets comprise session time values and the data processing system is configured to calculate the health trend indicator using said session time values and measurement data, whereby the health trend indicator is proportional to the rate of change of the said physiological changes of autonomic nervous system.

5. The system according to claim 1, wherein the data processing system is configured to
 determine a plurality of health indicators based on each measurement data set separately and associate a health-maintenance session time value to the health indicators determined,
 in said comparison, to determine if the health indicators have changed at a predefined rate using the reference indicator and the health-maintenance session time values.

6. The system according to claim 5, wherein the data processing system is configured to determine a temporal health trend indicator based on the separate health indicators and said time values associated therewith.

7. The system according to claim 6, wherein the data processing system is configured to
 collect at least one pre-monitoring data set during at least one first pre-monitoring health session before said health-maintenance sessions,
 use the pre-monitoring data set for determining said reference indicator.

8. The system according to claim 7, wherein said using of the pre-monitoring data set comprises at least one of:
 determining a pre-monitoring health indicator based on the at least one pre-monitoring data set and computing and storing the reference indicator based on the pre-monitoring health indicator,
 sending the pre-monitoring data or any value derived therefrom over a data network, and receiving the reference indicator associated with the pre-monitoring data over a data network.

9. The system according to claim 1, wherein the data processing system is further configured to perform at least one of:
 store the result of comparison of the at least one health indicator and the reference indicator,
 display the result of comparison of the at least one health indicator and the reference indicator,
 communicate over a data network the result of comparison of the at least one health indicator and the reference indicator.

10. The system according to claim 1, wherein the data processing system is further configured to
 store a session plan capable of containing session data including the timing and content of said health-maintenance sessions,
 and associate at least one of: said measurement data sets, health indicators, with said session data
 after said comparison of the at least one first health indicator with said reference indicator, to allow for changing of the session plan.

11. The system according to claim 1, wherein
the at least one sensor comprises a heart rate (HR) sensor,
the at least one physiological signal comprises a heart rate signal, and
the at least one health indicator comprises a heart rate variability (HRV) index.

12. The system according to claim 1, wherein
the at least one sensor comprises an electroencephalographic (EEG) sensor,
the at least one physiological signal comprises an EEG signal, and
the at least one health indicator comprises a brain activity index.

13. The system according to claim 1, further comprising a smartphone for providing auditory feedback, for the person during the measurement of the physiological signal based on the measurement data.

14. The system according to claim 1, wherein
the data processing system comprises a storage medium comprising software executable on a mobile computing device, the first software means being functionally connectable with said sensor, and
wherein the software comprises computer-executable instructions for performing said step of receiving.

15. The system according to claim 14, wherein the software further comprises computer-executable instructions for providing visual or auditory guidance for the person on conducting the health-maintenance sessions.

16. The system according to claim 14, wherein
the data processing system further comprises second software executable on a network data server, and
the first and second software are capable of exchanging data over a network connection, and
the second software comprises computer-executable instructions for performing at least one of the steps of storing, determining and comparing.

17. The system according to claim 14, wherein the data processing system further comprises user access control software, wherein said user access control software is capable of containing at least a first and second user access levels, wherein the first access level authorizes the person to initiate data collection for said health-maintenance sessions, and the second user access level authorizes another person to define said reference indicator and/or to set a session guidance for the person conducting the health-maintenance sessions.

18. The system according to claim 17, wherein the second user access level authorizes access to at least one of: the measurement data sets, the health indicators, the result of the comparison via a computer network.

19. The system according to claim 14, wherein the data processing system is further configured to
collect and analyze at least one of: measurement data sets, health indicators, from health-maintenance sessions of a plurality of different persons for obtaining population data,
and utilize the population data for determining the reference indicator.

20. A method of monitoring the health of a person, the method comprising
determining a session plan and storing the session plan in a non-transitory form within a data processing system, and
using at least one sensor capable of measuring at least one physiological signal generated by a autonomic nervous system of the person, measuring at least one physiological signal generated by the autonomic nervous system of the person during a plurality of consecutive health-maintenance sessions according to the session plan stored in a data processing system, and
collecting into the data processing system a plurality of measurement data sets corresponding to said health-maintenance sessions, and
operating the data processing system for
determining at last one first health indicator based on the measurement data sets, said at least one first health indicator being sensitive to physiological state of or changes in the autonomic nervous system, and
comparing the at least one first health indicator against predefined comparison criteria,
changing the session plan based on the outcome of the comparison,
wherein
the at least one first health indicator comprises a plurality of second health indicators separately determined based on each measurement data set and representing temporal variation of measurement data within said measurement data sets, and
the data processing system is operated to calculate the second health indicators based on
first measurement data contained in the first half of a measurement data set, corresponding to the first half of a single health-maintenance session, and
second measurement data contained in the second half of a measurement data set, corresponding to the second half of the single health-maintenance session,
wherein the health-maintenance session is a single meditation session, a single exercise session, or a single controlled breathing session.

21. The method according to claim 20, comprising collecting at least four measurement data sets from separate health-maintenance sessions over a period of at least four weeks, such as at least six sets over a period of six weeks.

22. The method according to claim 20, comprising
collecting at least one pre-monitoring data set during at least one first pre-monitoring health session before said health-maintenance sessions,
determining at least one reference indicator based on the pre-monitoring data set,
collecting said measurement data sets, and
using the reference indicator as part of said comparison criteria.

23. The method according to claim 20, wherein the data processing system comprises at least two user accounts having access to monitoring data of the person, the first user account allowing collection and storage of measurement data sets and the second user account allowing reading of measurement data sets and/or health indicators, and the method comprises
collecting and storing said data sets using the first user account,
reading measurement data sets and/or health indicators derived therefrom using the second user account, and
changing the session plan using the second user account.

24. A method of treating autonomic nervous system related dysfunctions of a person,
providing at least one sensor capable of measuring at least one physiological signal generated by the autonomic nervous system of the person,
providing a data processing system capable of storing and processing measurement data provided by the sensor,
operating the sensor and data processing system during a plurality of health-maintenance monitoring sessions according to a session plan for collecting measurement data sets corresponding to said monitoring sessions, determining at last one first health indicator based on the measurement data sets, the at least one first health indicator being sensitive to physiological state of or changes in the autonomic nervous system, and determining if the temporal development of the at least one first health indicator fulfills predefined criteria, and, in the affirmative, changing the session plan, operating the sensor and data processing system during a plurality of further health-maintenance sessions according to the changed session plan for collecting further measurement data sets corresponding to said further sessions wherein the at least one first health indicator comprises a plurality of second health indicators separately determined based on each measurement data set and representing temporal variation of measurement data within said measurement data sets, and the data processing system is operated to calculate the second health indicators based on first measurement data contained in the first half of a measurement data set, corresponding to the first half of a single health-maintenance session, and second measurement data contained in the second half of a measurement data set, corresponding to the second half of the single health-maintenance session, wherein the health-maintenance session is a single meditation session, a single exercise session, or a single controlled breathing session.

25. The method according to claim 24, comprising before operating the sensor and data processing system for the monitoring sessions, operating the sensor and data processing system during at least one pre-monitoring session for collecting at least one pre-monitoring data set, and determining said predefined criteria based on said at least one pre-monitoring data set.

26. The method according to claim 24, wherein said changing of the session plan comprises changing the timing of sessions, the duration of sessions or the content of the sessions.

* * * * *